(12) United States Patent
Arnalot i Aguilar et al.

(10) Patent No.: US 6,506,941 B1
(45) Date of Patent: Jan. 14, 2003

(54) VENLAFAXINE PRODUCTION PROCESS

(75) Inventors: Carmen Arnalot i Aguilar, Girona (ES); Jordi Bosch i Lladó, Girona (ES); Pelayo Camps Garcia, Barcelona (ES); Maria del Carmen Onrubia Miguel, Barcelona (ES); Núria Soldevilla Madrid, Barcelona (ES)

(73) Assignee: Medichem, S.A., Barcelona (ES)

( * ) Notice: Subject to any disclaimer, the term of this patent is extended or adjusted under 35 U.S.C. 154(b) by 0 days.

(21) Appl. No.: 10/048,107

(22) PCT Filed: Jul. 17, 2000

(86) PCT No.: PCT/ES00/00255

§ 371 (c)(1), (2), (4) Date: Jan. 25, 2002

(87) PCT Pub. No.: WO01/07397

PCT Pub. Date: Feb. 1, 2001

(30) Foreign Application Priority Data

Jul. 27, 1999 (ES) ................................................ 9901686

(51) Int. Cl.$^7$ ............................................ C07C 215/00
(52) U.S. Cl. ...................................... 564/355; 564/338
(58) Field of Search .................................. 564/355, 336

Primary Examiner—Samuel Barts
(74) Attorney, Agent, or Firm—Scully, Scott, Murphy & Presser

(57) ABSTRACT

A process for the preparation of venlafaxin and/or the physiologically acceptable addition salts thereof that consists of reacting a compound of general formula (II) where R is a $C_1$–$C_{10}$ alkyl, aryl, aralkyl or cycloalkyl group of 3 to 6 atoms of carbon, with a organomagnesium compound of general formula (III) where X is an atom of halogen and, if desired, a salt of the thus obtained venlafaxin is formed by reaction thereof with a physiologically acceptable acid.

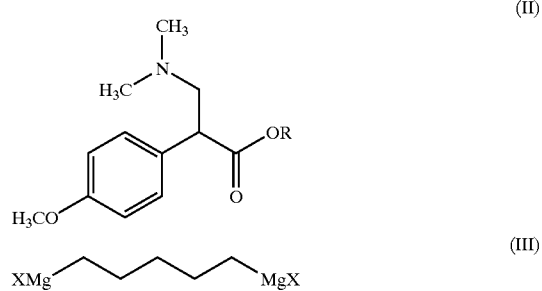

7 Claims, No Drawings

VENLAFAXINE PRODUCTION PROCESS

This application is a 371 of PCT/ES00/00255 filed Jul. 17, 2000.

DESCRIPTION

1. Field of the Art

The present invention refers to a new process for the preparation of venlafaxin, which is an antidepressant and is the international non-proprietary name (INN) for (±)-1-[2-(dimethylamino)-1-(4-methoxyphenyl)ethyl]cyclohexanol, and/or the physiologically acceptable addition salts thereof.

2. Prior Art Reference

Venlafaxin, of formula

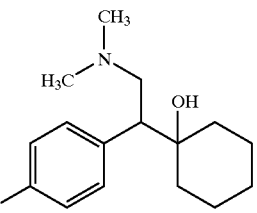

(I)

as well as processes for the preparation thereof, are described in the document U.S. Pat. No. 4,535,186 and it is usually marketed as the hydrochloride of the racemic form thereof.

In the Spanish documents ES-A-527938 and ES-A-544402 and in document U.S. Pat. No. 4,535,186 giving priority thereto, several processes for the preparation of venlafaxin are described. Other processes are also described in J. P. Yardley et al. J. MED. Chem. 1990. 33:2899–2905 and in the document U.S. Pat. No. 5,043,466.

The processes for the preparation of venlafaxin described in the afore-mentioned documents may be represented as shown in Scheme 1 of reaction sequences.

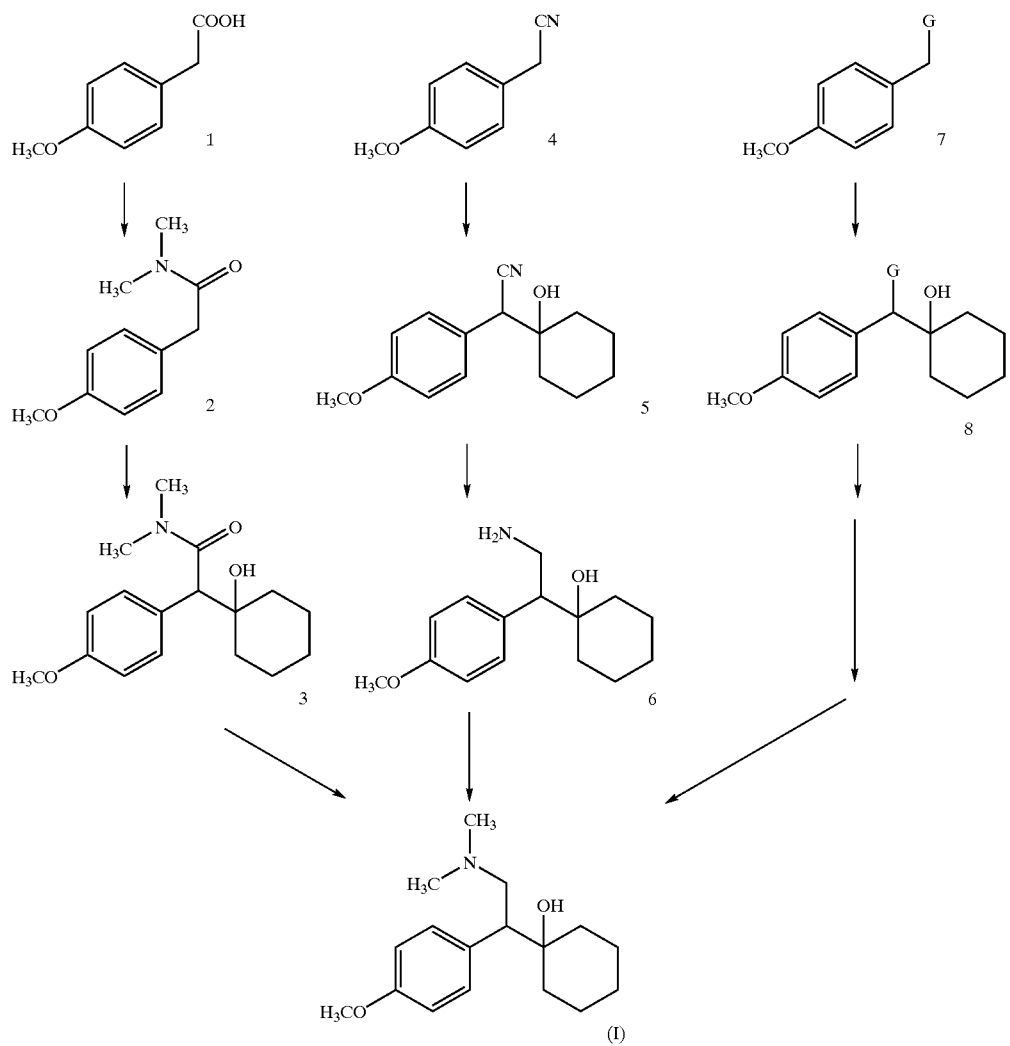

Scheme 1

In the document ES-A-527938 and in the document U.S. Pat. No. 4,535,186, as well as in the article of J. P Yardley et al., the process is described which consists of preparation the amide 2, starting out from the carboxylic acid 1, to introduce in said amide the cyclohexanol residue by means of the formation of an enolate anion, by reacting with n-butyl-lithium, and later condensation of said enolate anion with cyclohexanone, giving place to the amide 3 which is reduced to give venlafaxin.

On the other hand, in the document ES-A-544402, as well as in the document U.S. Pat. No. 4,535,186 and in the article of J. P. Yardley et al., a alternative process is described consisting of introducing the cyclohexanol residue in the nitrilo 4, in the same way as in the previous case, to obtain the intermediate 5 that is reduced to the amine 6 by catalytic hydrogenation with a catalyst such as, for example, 5% rhodium on alumina. In this case, the final stage consists of the double methylation of the amine 6 to obtain venlafaxin, although appreciable amounts of a by-product, of formula

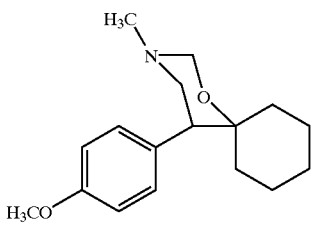

are formed during said reaction that should be reduced under more energetic conditions to lead to the preparation of venlafaxin.

In the document U.S. Pat. No. 4,535,186 a very similar path is also described which starts out from a starting product 7, in which the group G can be —COOH, —COO⁻, –COOR (R being alkyl), —CHO and —CH$_2$OH, so as, using the same strategy already commented upon, to introduce the cyclohexanol residue and later, in a variable number of stages that depends on the nature of the group G selected, to convert the intermediate 8 into venlafaxin.

On the other hand, in the document U.S. Pat. No. 5,043,466, a variant of the last two ways mentioned is described consisting of conducting the reaction of introduction of the cyclohexanol residue using a selection of certain hydrocarbon solvents and using groups G such as nitrilo, N,N-dimethylamido and N,N-dimethylthioamido.

As may be appreciated, all the above well-known processes share the same strategy of synthesis, consisting of introducing the cyclohexanol residue by condensation of cyclohexanone with an enolate anion of an arylacetic acid, or of a synthetic analogue thereof, and subsequently to modify the carboxylic group derivative or analogue thereof, to convert it into the N,N-dimethylaminomethyl group.

All the abovementioned cases are complicated time-consuming processes which, furthermore, are not very appropriate industrially, since necessarily require the use of a strong base, such as n-butyl-lithium, to form the enolate anion and, therefore, the use of rigorously anhydrous reaction conditions, inert atmosphere, and very low reaction temperatures.

There still remains, therefore, the need to have new alternative processes for the preparation of venlafaxin that are simpler and of easier industrial adaptation.

OBJECT OF THE INVENTION

The object of the present invention is a process for the preparation of venlafaxin of easy industrial adaptation based on the use of easily obtainable starting products and intermediates.

DESCRIPTION OF THE INVENTION

The process of the present invention for the preparation of venlafaxin and/or the physiologically acceptable addition salts thereof, consists essentially of reacting a compound of general formula (II)

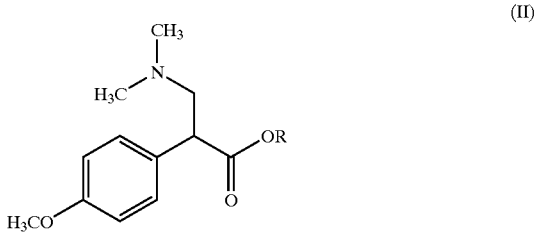

where R is a $C_1$–$C_{10}$ alkyl, aryl, aralkyl or cycloalkyl group of 3 to 6 atoms of carbon, with a organomagnesium compound of general formula (III)

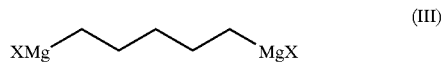

where X is an atom of halogen, preferably bromine and, if desired, a salt of the thus prepared venlafaxin is formed by reaction thereof with a physiologically acceptable acid.

The compound of formula (II) may be prepared by conventional methods, well-known to the man of the art, among which may be mentioned those which are reflected in the reaction sequences of Scheme 2 starting out from p-methoxyphenylacetic esters.

Scheme 2

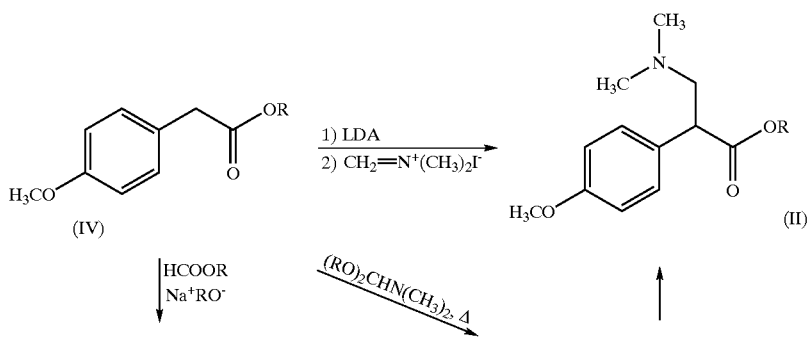

-continued

As shown in Scheme 2, the ester (IV) may be reacted with dimethylformamide dialkylacetal to give place to a β-(N,N)-dimethylamino)-α-(p-methoxyphenyl)acrylic ester (VI), which can be reduced, either by metallic hydrides such as NaBH₄ or LiAlH₄ or by catalytic hydrogenation, to give the compound (II).

The intermediate (VI) can also be thus obtained by formylation of the ester (IV) to give place to the intermediate (V), followed by the reaction of said intermediate (V) with dimethylamine.

If desired, although it is not necessary to follow this alternative, which is not the preferred one, it is also possible to prepare compound (II) directly from the ester (IV) by formation of the enolate anion thereof, for example with lithium diisopropylamide (LDA), followed by reaction of said enolate anion with an appropriate Eschenmosher salt, for example N,N-dimethylmethyleneimmonium iodide.

As far as the organomagnesium compounds of formula (III) are concerned, can be acquired on the marketplace, such as for example in the preferred case of pentamethylene-1,5-bis(magnesium bromide), or can be easily prepared from the corresponding 1,5-dihalopentane by reaction with magnesium in an inert solvent, such as tetrahydrofuran.

Compound (II) and the organomagnesium compound (III) may be reacted in an inert solvent, an inert solvent being understood to be any that in the opinion of the man of the art does not substantially react with the reactants involved. Preferred among the inert solvents are the non-cyclic and cyclic ethers, with diethyl ether, tetrahydrofuran, dioxane, etc. being particularly preferred.

The most appropriate reaction temperatures are those ranging from 0° C. to the reflux temperature of the selected solvent.

Once the venlafaxin base has been prepared, if desired it can be converted, by way of conventional techniques known to the man of the art, into an addition salt with an physiologically acceptable inorganic or organic acid, among which there may be cited without limitative character: hydrochloric, sulfuric, phosphoric, methanesulfonic, p-toluenesulfonic, citric, maleic, malic, fumaric, etc. acids. It is preferred to use hydrochloric acid as the physiologically acceptable acid to form the venlafaxin addition salt.

The following examples are given for the purpose of providing the man of the art with a sufficiently clear and complete explanation of the present invention, but should not be considered as limitations to the essential aspects of the object thereof, as have been disclosed in the foregoing paragraphs hereof.

EXAMPLES

Example 1

Preparation of ethyl p-methoxyphenylacetate (IV; R=Et)

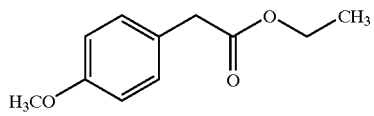

10 g (0.06 mol) of p-methoxyphenylacetic acid, 30 ml (0.74 mol) of ethanol and 0.11 ml (0.0026 mol) of sulfuric acid were mixed in a 250 ml balloon flask provided with thermometer and reflux cooler. The thus obtained solution was heated to reflux (78° C.) and held for 1 hour 20 minutes. It was then cooled down at room temperature and 50 ml of deionized water were added. The ethanol was evaporated under vacuum and 40 ml of dichloromethane were added over the residual aqueous phase. The thus obtained mixture was stirred and allowed to decant. The organic phase was washed with 30 ml of a sodium bicarbonate saturated solution, was dried and filtered under vacuum. After evaporating the dichloromethane under vacuum, a colorless residue of ethyl p-methoxyphenylacetate weighing 10.41 g was obtained (Yield: 89%)

Example 2

Preparation of ethyl α-formyl-p-methoxyphenylacetate (V; R=Et)

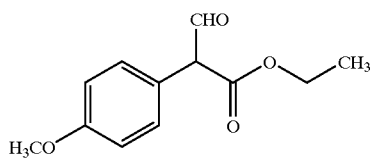

20 g (0.109 mol) of ethyl p-methoxyphenylacetate and 58.0 g (0.721 mol) of ethyl formate were mixed in a 500 ml balloon flask provided with magnetic stirring and thermometer under a gentle nitrogen flow. The thus obtained solution was cooled to 0–5° C. and 8.88 g (0.222 mol) of 60% sodium hydride were added in portions, over 3 hours 30 minutes. After the last addition of sodium hydride, stirring was continued for 2 hours and 30 minutes at room temperature. It was cooled again to 0–5° C. and 100 ml of deionized water were added slowly, at an internal temperature not above 20° C. After adjusting the pH to between 5–6 by addition of 5N hydrochloric acid, 200 ml of dichloromethane were added, the mixture was stirred and the phase were allowed to decant. The aqueous phase was extracted with 100 ml of dichloromethane again, the dichloromethane extracts were pooled and were washed with 100 ml of deionized water. After decanting, the organic phase was dried with sodium sulfate, was filtered and the dichloromethane was evaporated to dryness under vacuum. A yellowish residue of ethyl α-formyl-p-methoxyphenyl acetate weighing 22.45 g was obtained (Yield: 98%)

Example 3

Preparation of ethyl α-(p-methoxyphenyl)-β-(dimethylamino)acrylate (VI; R=Et)

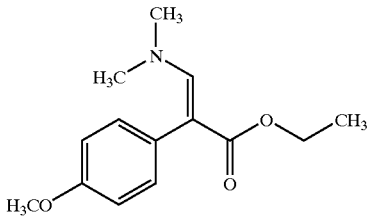

21 g (0.0945 mol) of ethyl α-formyl-p-methoxyphenylacetate, 80 ml of ethanol and 31,1 g (0.38 mol) of dimethylamine hydrochloride were mixed in a 250 ml balloon flask provided with magnetic stirring and thermometer under a gentle nitrogen flow. Subsequently 7.4 g (0.054 mol) of potassium carbonate were added. The thus obtained solution was stirred at room temperature for 3 days. The solvent was evaporated to dryness in the rotary evaporator and 120 ml of water were added over the thus obtained solid residue. The pH was adjusted to 5–6 with 5N hydrochloric acid and the product of the aqueous phase was extracted with 2×80 ml of dichloromethane. The organic extracts were dried with sodium sulfate and the solvent was removed under vacuum, to give a residue weighing 23.26 g and solidifying at room temperature (Yield: 98.7%)

Example 4

Preparation of ethyl α-(p-methoxyphenyl)-β-(dimethylamino)acrylate (VI; R=Et) (via dimethylformamide diethylacetal)

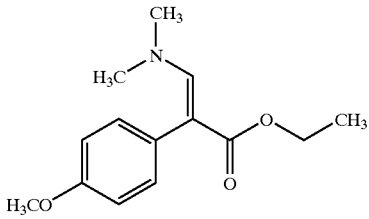

2 g (0.0103 mol) of ethyl p-methoxyphenylacetate and 9.1 g (10.6 ml, 0.0618 mol) of dimethylformamide diethylacetal were mixed in a 100 ml balloon flask provided with reflux cooler, magnetic stirring and thermometer. The thus obtained solution was heated to reflux (135° C.) for 20 hours. Then the dimethylformamide diethylacetal and the unreacted ethyl p-methoxyphenylacetate were removed by distillation under vacuum, the desired product being obtained as distillation residue. 2,14 g of ethyl α-(p-methoxyphenyl)-β-(dimethylamino)acrylate were thus obtained (Yield: 83%).

Example 5

Preparation of ethyl α-(p-methoxyphenyl)-β-(dimethylamino)propionate (II; R=Et)

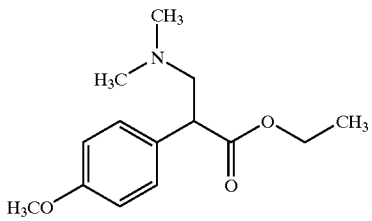

A gentle nitrogen flow was applied to a 100 ml balloon flask provided with magnetic stirring and 0.455 g (0.0120 mol) of sodium borohydride was mixed with 10 ml of ethanol. Thereafter, 1 g (0.0040 mol) of ethyl α-(p-methoxyphenyl)-β-(dimethylamino)acrylate was added. The mixture was stirred for 24 hours at room temperature and then 3 ml of water were added. The ethanol was removed in the rotary evaporator and 20 ml of water and 20 ml of dichloromethane were added over the residue. The mixture was stirred and the phases were separated. The process continued with the organic phase. 20 ml of water were added, the mixture was acidified to acid pH and decanted. The aqueous phase was washed with 20 ml of dichloromethane and was then basified to basic pH. The product was extracted from the aqueous phase with 20 ml of dichloromethane. It was dried with sodium sulfate, was filtered and the solvent was removed under vacuum to give 0.21 g of ethyl α-(p-methoxyphenyl)-β-(dimethylamino)propionate (Yield: 21%).

Example 6

Preparation of ethyl α-(p-methoxyphenyl)-β-(dimethylamino)propionate (II; R=Et)

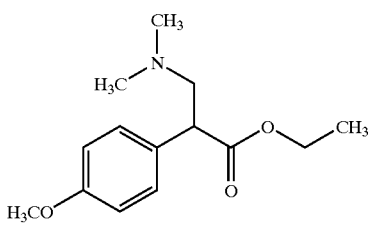

4.645 g (0.0186 mol) of ethyl α-(p-methoxyphenyl)-β-(dimethylamino)acrylate were dissolved in 225 ml of ethanol in a 1 liter glass reactor, 7,46 g of Pt/C type 18 catalyst were added (4.83% Pt and 59.70% water) and a pressure of 200 psi of $H_2$ was applied. The mixture was left hydrogenating for 3 days, after which it was filtered through Celite® 535 and was washed with 2×40 ml of ethanol. The ethanol was then removed under vacuum, to give a residue weighing 0.72 g. The residue was suspended in 40 ml of 2N hydrochloric acid and was washed with dichloromethane. The operation continued with the acid aqueous phase which was basified with a mixture of sodium carbonate and potassium carbonate (1/1) to pH 11 and the product was extracted with 4×40 ml of dichloromethane. The pooled organic phases were dried with sodium sulfate, were filtered and were evaporated to dryness under vacuum, to give a pale yellow oil weighing 3.82 g corresponding to ethyl α-(p-methoxyphenyl)-β-(dimethylamino)propionate (Yield: 82%).

Example 7

Preparation of methyl α-(p-methoxyphenyl)-β-(dimethylamino)propionate (II; R=Me)

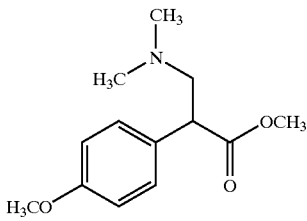

A gentle nitrogen flow was bubbled through a 100 ml balloon flask provided with thermometer and magnetic stirring, and 1 g (5.55 mmol) of methyl p-methoxyphenylacetate was dissolved in 10 ml of tetrahydrofuran. The mixture was cooled to −35° C. and 2.77 ml (5.55 mmol) of 2M LDA (lithium diisopropylamide) in tetrahydrofuran/heptane/ethylbenzene solution were added over 10 minutes. Stirring was continued for a further hour at a temperature ranging from −35° C. to −40° C. Then 2.15 g (0.01165 mol) of N,N-dimethylmethyleneimmonium iodide were added over 20 minutes at −40° C. The mixture was then allowed to reach the room temperature and was stirred for a further 17 hours.

After adding 2 ml of water, the tetrahydrofuran was removed by evaporation under vacuum at room temperature. 25 ml of water were charged and the mixture was acidified to acid pH. The aqueous solution was washed with 20 ml of dichloromethane and, after decanting, the aqueous phase was basified with aqueous sodium hydroxide to pH 12–13. The product was extracted with 1×20 ml of dichloromethane. After drying with sodium sulfate, filtering and removal of the solvent by evaporation under vacuum, a residue was obtained weighing 0.26 g corresponding to methyl α-(p-methoxyphenyl)-β-(dimethylamino)propionate (Yield: 19.7%)

Example 8

Preparation of ethyl α-(p-methoxyphenyl)-β-(dimethylamino)propionate (II; R=Et)

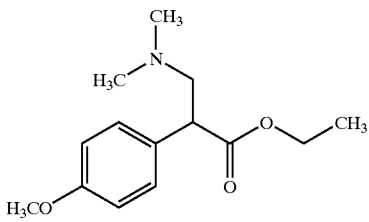

A gentle nitrogen flow was applied to a 1 L balloon flask provided with magnetic stirring and 6.06 g (0.159 mol) of aluminum and lithium hydride was mixed with 300 ml of tetrahydrofuran. The suspension was cooled to −5°/0° C. and a solution formed by 20 g (0.08 mol) of ethyl α-(p-methoxyphenyl)-β-(dimethylamino)acrylate prepared according to Example 3 and 75 ml of tetrahydrofuran was added. The mixture was stirred at −5/0° C. for 7 hours and was then held at room temperature o.n. (14 hours).

It was then cooled to 0–10° C., 75 ml of water were added slowly and the tetrahydrofuran was removed by evaporation in the rotary evaporator. 300 ml of deionized water and 350 ml of dichloromethane were added over the thus obtained solid residue. The mixture was filtered through a Celite pre-layer and decanted. The organic phase was dried with sodium sulfate and evaporated to dryness in the rotary evaporator. 13.68 g of residue were obtained in form of a yellowish oil corresponding to ethyl α-(p-methoxyphenyl)-β-(dimethylamino) propionate (Yield: 68%).

Example 9

Preparation of ethyl α-(p-methoxyphenyl)-β-(dimethylamino)propionate (II; R=Et)

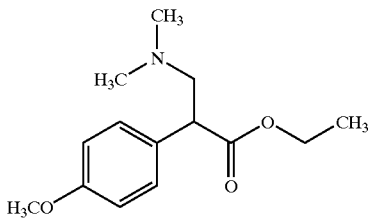

19.8 g (0.0795 mol) of ethyl α-(p-methoxyphenyl)-β-(dimethylamino)acrylate were dissolved in 740 ml of ethanol, in a 1 liter glass reactor, 30.6 9 of Pt/C type 18 catalyst (4.83% Pt and 59.70% water) were added, the mixture was first purged with nitrogen and then with hydrogen and finally a pressure of 600 psi $H_2$ was applied. The mixture was left hydrogenating for 23 hours, was then filtered through Celite® 535 and was washed with 2×165 ml of ethanol. The ethanol was then removed under vacuum. The residue was dissolved in 30 ml of dichloromethane and was extracted with 50 ml and 2×15 ml of 2N hydrochloric acid. The operation continued with the acid aqueous phase that was basified with 40 ml of aqueous sodium hydroxide solution to pH 11. The product was extracted with 4×35 ml of ethyl acetate. The pooled organic phases were dried with sodium sulfate, filtered and evaporated to dryness under vacuum to give a pale yellow oil weighing 14.7 g, corresponding to ethyl α-(p-methoxyphenyl)-β-(dimethylamino) propionate (Yield: 74%).

Example 10

Preparation of 1-[2-(dimethylamino)-1-(p-methoxyphenyl)ethyl]cyclohexanol hydrochloride (I) (venlafaxin hydrochloride)

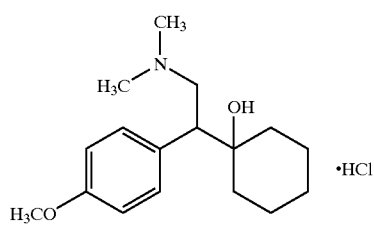

A gentle nitrogen flow was applied to a 500 ml balloon flask provided with cooler, thermometer and magnetic stirring and 86.0 ml (0.043 mol) of a solution of pentamethylene bis(magnesium bromide) in 0.5 M tetrahydrofuran solution was charged, it was cooled to 10–20° C. and 8.5 g (0.0338 mol) of ethyl α-(p-methoxyphenyl)-β-(dimethylamino) propionate prepared as described in Example 6 were added over 30 minutes and and the mixture was stirred at room temperature for 3 hours 30 minutes. It was then cooled to 0–10° C. and 50 ml of water were added slowly, the tetrahydrofuran was removed by evaporation under vacuum, 120 ml of water were added and the mixture was basified to pH 12–13 with 5.5 ml of 50% sodium hydroxide. Then 170 ml of dichloromethane were added, the insoluble material was removed by filtration and the phases were separated. The organic phase was evaporated to dryness under vacuum and 10.25 g of residue were obtained. Then 50 ml of ethyl acetate and 3.4 ml of ethanol-10.8N hydrochloric acid were added. The precipitated white solid was filtered and was dried to constant weight to give 4.54 g of 1-[2-(dimethylamino)-1-(methoxyphenyl)ethyl]cyclohexanol hydrochloride (venlafaxin) (Yield: 42.8%)

What is claimed is:

1. A process for the preparation of venlafaxin and/or the physiologically acceptable addition salts thereof, characterized in that a compound of general formula (II)

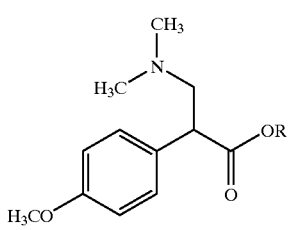

(II)

where R is a $C_1$–$C_{10}$ alkyl, aryl, aralkyl or cycloalkyl group of 3 to 6 atoms of carbon, is reacted with a organomagnesium compound of general formula (III)

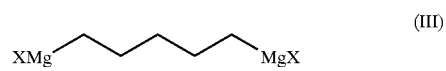

(III)

where x is an atom of halogen and, if desired, a salt of the thus obtained venlafaxin is formed by reaction thereof with a physiologically acceptable acid.

2. The process of claim 1, characterized in that the organomagnesium compound is pentamethylene-1,5-bis (magnesium bromide).

3. The process of claim 1 or claim 2, characterized in that compound (II) is reacted with the organomagnesium compound (III) in a solvent of the type of acyclic and/or cyclic ethers.

4. The process of claim 3, characterized in that the solvent is selected from the group formed by diethyl ether, tetrahydrofuran and dioxane.

5. The process of claim 3, characterized in that the reaction is performed at a temperature from 0° C. to the reflux temperature of the solvent.

6. The process of claim 1, characterized in that the physiologically acceptable acid to form the addition salt is selected from hydrochloric acid, sulfuric acid, phosphoric acid, methanesulfonic acid, ptoluenesulfonic acid, citric acid, maleic acid, malic acid and fumaric acid.

7. The process of claim 6, characterized in that the physiologically acceptable acid selected is hydrochloric acid.

* * * * *